US008993972B2

(12) United States Patent
Rao et al.

(10) Patent No.: US 8,993,972 B2
(45) Date of Patent: Mar. 31, 2015

(54) FLUORESCENCE BASED SENSORS UTILIZING A MIRRORED CAVITY

(75) Inventors: Govind Rao, Columbia, MD (US); Hung Lam, Baltimore, MD (US); Yordan Kostov, Columbia, MD (US); Leah Tolosa, Columbia, MD (US); Xudong Ge, Ellicott City, MD (US)

(73) Assignee: University of Maryland Baltimore County, Baltimore, MD (US)

( * ) Notice: Subject to any disclaimer, the term of this patent is extended or adjusted under 35 U.S.C. 154(b) by 1407 days.

(21) Appl. No.: 12/692,752

(22) Filed: Jan. 25, 2010

(65) Prior Publication Data

US 2010/0207035 A1    Aug. 19, 2010

Related U.S. Application Data

(60) Provisional application No. 61/146,771, filed on Jan. 23, 2009.

(51) Int. Cl.
*G01T 1/20*    (2006.01)
*G01N 21/64*    (2006.01)

(52) U.S. Cl.
CPC .................................. *G01N 21/645* (2013.01)
USPC ................... 250/368; 250/361 R; 250/363.01

(58) Field of Classification Search
CPC ....... G01N 21/64; G01N 23/22; G01N 21/84; G01N 21/031; G01N 21/256; G01N 21/85
USPC ........... 250/458.1, 363.01, 461.2, 368, 361 R
See application file for complete search history.

(56) References Cited

U.S. PATENT DOCUMENTS

| | | | | |
|---|---|---|---|---|
| 2005/0046834 A1* | 3/2005 | Gilby | ............................ | 356/317 |
| 2005/0090014 A1* | 4/2005 | Rao et al. | ...................... | 436/166 |
| 2006/0054500 A1* | 3/2006 | Kaschak | ....................... | 204/400 |
| 2006/0197034 A1* | 9/2006 | Shirai et al. | ................ | 250/458.1 |
| 2007/0212681 A1* | 9/2007 | Shapiro et al. | .................... | 435/5 |
| 2009/0079988 A1* | 3/2009 | Narahara et al. | .............. | 356/445 |

* cited by examiner

*Primary Examiner* — David Porta
*Assistant Examiner* — Carolyn Igyarto
(74) *Attorney, Agent, or Firm* — Rene A. Vazquez, Esq.

(57) ABSTRACT

A fluorescence based sensor system that provides improved signal-to-noise over prior systems is provided. The system includes a fluorescence based sensing medium that is contained a recessed cavity with reflective sides that allow for more uniform excitation of the fluorescence based sensing medium by the excitation light.

26 Claims, 5 Drawing Sheets

FLUORESCENCE BASED SENSORS UTILIZING A MIRRORED CAVITY

This application claims priority to U.S. Provisional Application Ser. No. 61/146,771, filed Jan. 23, 2009, whose entire disclosure is incorporated herein by reference.

BACKGROUND OF THE INVENTION

1. Field of the Invention

The present invention relates to fluorescence based sensors and, more particularly, to fluorescence based sensors with mirrored cavities for improved sensitivity.

2. Background of the Related Art

Pollution is one of the major problems in the modern industrialized world. In the United States, industry is the greatest source of pollution, accounting for more than half the volume of all water pollution and for the most deadly pollutants. Some 370,000 manufacturing facilities use huge quantities of freshwater to carry away wastes of many kinds. The waste-bearing water is discharged into streams, lakes, or oceans. In its National Water Quality Inventory, the U.S. Environmental Protection Agency concluded that approximately 40% of the nation's surveyed lakes, rivers, and estuaries were too polluted for such basic uses as drinking supply, fishing, and swimming. Pollution not only increases the concentrations of harmful substances, but also changes the pH and the levels of CO2 and oxygen dissolved in a body of water, thereby disrupting the water's ecological balance, killing off some plant and animal species while encouraging the overgrowth of others.

Another environmental problem is global warming. The majority of scientists studying climate changes believe that global warming is likely caused by increasing amount of greenhouse gases (mostly $CO_2$) discharged into the environment by human activity. Global warming has numerous deleterious effects, such as rising sea levels, changing the amount and pattern of precipitation, and increasing the intensity of extreme weather events and changing agricultural yields. The rise in $CO_2$ levels, while contributing to global warming, is also creating ocean acidification at an alarming rate as the oceans collect more $CO_2$. Warming water and increasingly acidic seas will further change the global ecosystem.

Scientists studying the association between Earth climate and extinctions stated that "the global temperatures predicted for the coming centuries may trigger a new 'mass extinction event', where over 50 percent of animal and plant species would be wiped out." Many of the species especially at risk are Arctic and Antarctic fauna because those species usually rely on cold weather conditions to survive and to reproduce. This will adversely affect the existing local fisheries upon which humans depend. Additionally, it has been shown that climate change due to increases in carbon dioxide concentration is largely irreversible for 1,000 years after emissions have stopped. Concerted action is required to minimize the effect of global warming and most national governments have signed and ratified the Kyoto Protocol aimed at reducing greenhouse gas emissions.

Meanwhile, governments are in the process of implementing requirements for systems to monitor $pCO_2$ levels and for alleviating the severity of the effects of global warming. Therefore, there is currently an urgent need for small, low-cost, calibration-free $pCO_2$ sensing systems for ocean monitoring.

SUMMARY OF THE INVENTION

An object of the invention is to solve at least the above problems and/or disadvantages and to provide at least the advantages described hereinafter.

Therefore, an object of the present invention is to provide sensitive fluorescence based sensors.

Another object of the present invention is to provide sensitive, low cost, small pH, $pCO_2$ and $pO_2$ sensors.

To achieve at least the above objects, in whole or in part, there is provided a fluorescence based sensor, comprising a fluorescence based sensing medium having a top surface, a bottom surface and at least one side surface, a reflective surface adjacent to the at least one side surface of the fluorescence based sensing medium, wherein the reflective surface is positioned to reflect excitation light that enters the fluorescence based sensing medium through the at least one side surface and that passes through the fluorescence based sensing medium back into the fluorescence based sensing medium, and a detector positioned to detect fluorescence emissions that exit through one of either the bottom or top surface of the fluorescence based sensing medium.

To achieve at least the above objects, in whole or in part, there is also provided a fluorescence based sensor, comprising a housing, a recessed cavity formed in the housing, wherein at least one of the sides of the recessed cavity are reflective, a fluorescence based sensing medium positioned in the recessed cavity, an opening in the housing that extends from a side surface of the housing to the recessed cavity for allowing excitation light originating outside the housing to enter the fluorescence based sensing medium in the recessed cavity and a detector positioned to detect fluorescence emissions that exit through a bottom surface of the fluorescence based sensing medium, wherein the housing material between the fluorescence based sensing medium and a bottom surface of the housing is at least partially transparent to fluorescence emissions from the fluorescence based sensing medium.

To achieve at least the above objects, in whole or in part, there is also provided a fluorescence based sensor system, comprising a fluorescence based sensing medium having a top surface, a bottom surface and at least one side surface a reflective surface adjacent to the at least one side surface of the fluorescence based sensing medium, wherein the reflective surface is positioned to reflect excitation light that enters the fluorescence based sensing medium through the at least one side surface and that passes through the fluorescence based sensing medium back into the fluorescence based sensing medium a detector positioned to detect fluorescence emissions that exit through one of either the bottom or top surface of the fluorescence based sensing medium, and an excitation source for generating excitation light and directing the excitation light towards a side surface of the fluorescence based sensing medium.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Conventional sensors for environment monitoring usually require frequent sampling from the environment being monitored, and then analyzing the samples in a lab or station. This requires a significant labor and is inconvenient for sample handling and transport.

Autonomous monitors can be deployed on seas, rivers, lakes, or any other open water bodies with only minimal human intervention. Data obtained from the system can be transmitted to a monitoring station wirelessly or via a satellite. The fluorescence based sensors of the present invention can be made inexpensively, and will allow sensor systems to be built on many satellite-tracked drifters to obtain, for example, $pCO_2$ concentration patterns in an area. Thousands of sensor systems can be deployed worldwide to monitor the overall patterns of ocean acidification.

The present invention provides a low cost sensing system that can measure both chlorophyll concentration and turbidity. The present system would is useful for monitoring the health of coastal areas and ecosystems, such as the Chesapeake Bay.

Figure 1A:
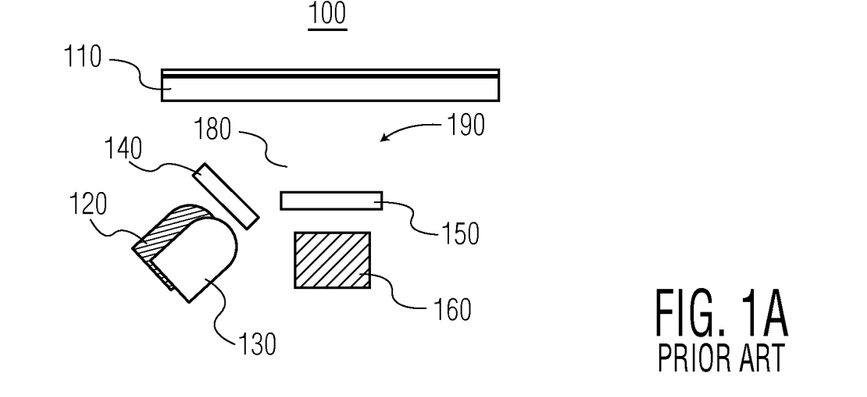
FIGS. 1A is a schematic diagram of a related art pH fluorescence sensor system.

FIG. 1A shows a related art pH fluorescence sensor system 100. The system 100 includes a sensor patch 110, a violet LED 120, a blue LED 130, an excitation filter 140, an emission filter 150 and a detector 160. The sensor patch is typically thin, usually less than approximately 0.5 mm thick, so as to provide response times on the order of 2-3 minutes or less. In operation, the sensor patch 110 is illuminated by a first of the two LEDs (e.g., the violet LED 120), and the pH dependent fluorescence emission is measured by detector 160. The sensor patch is then illuminated by the second of the two LEDs (e.g., the blue LED 130) and the resulting pH dependent fluorescence emission is measured by detector 160. The ratio of the fluorescence emissions resulting from excitation by each of the two LEDs is calculated and pH data is determined from a calibration curve.

Figure 1B:
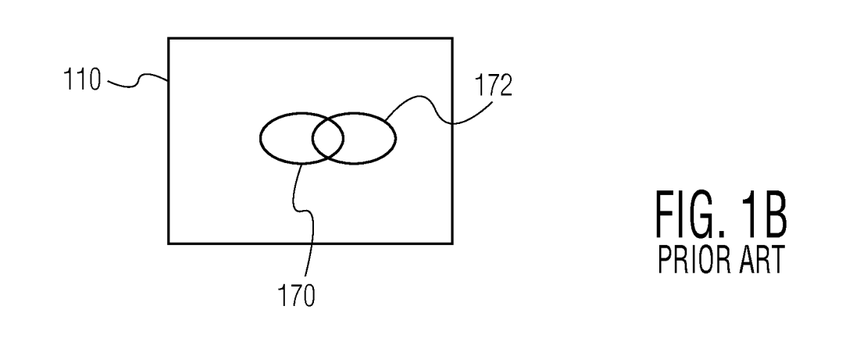
FIG. 1B is a bottom view of the sensor patch of FIG. 1A, showing the violet LED illumination region and the blue LED illumination region.
Figure 1C:
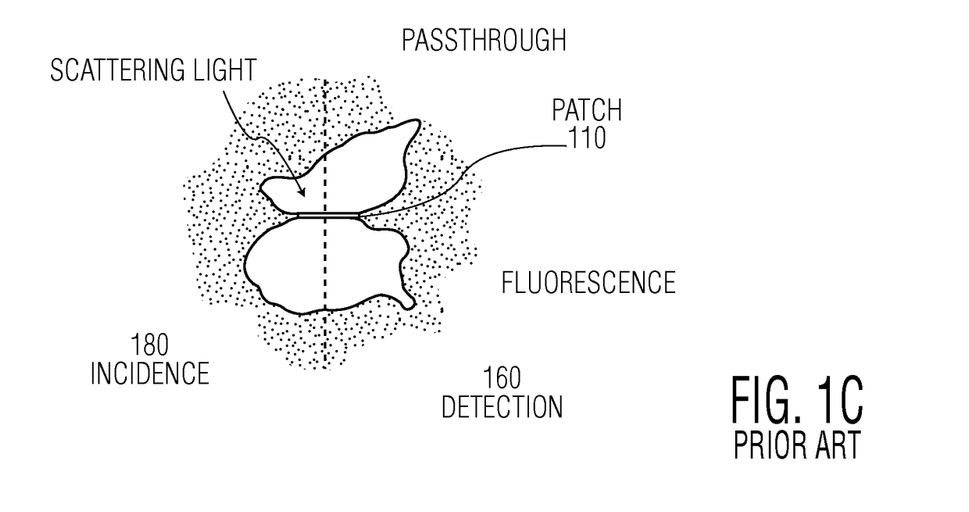
FIG. 1C is a schematic diagram showing the distribution of scattered excitation light and fluorescence light for the system of FIG. 1A.

The system 100 has limitations. In this geometry, the violet LED 120 and the blue LED 130 illuminate slightly different areas of the sensor patch 110 due to the spatial separation between the two LEDs. This is illustrated in FIG. 1B, which is a bottom view of the sensor patch 110, showing the violet LED illumination region 170 and the blue LED illumination region 172. Further, the geometry of system 100 is not the ideal 90 degree separation between the excitation light 180 and the emission light 190. This leads to significant scattered emission light reaching the detector 160. Even if the LEDs 120, 130 and detector 160 of system 100 where positioned at 90 degrees with respect to each other, the geometry of system 100 inherently produces a lot of scattered light that propagates towards the detector 160, as shown in FIG. 1C. FIG. 1C is a schematic diagram showing the distribution of scattered light and fluorescence light for the geometry of system 100. As shown in FIG. 1C, a significant amount of scattered light reaches the detector 160.

Figure 2A:
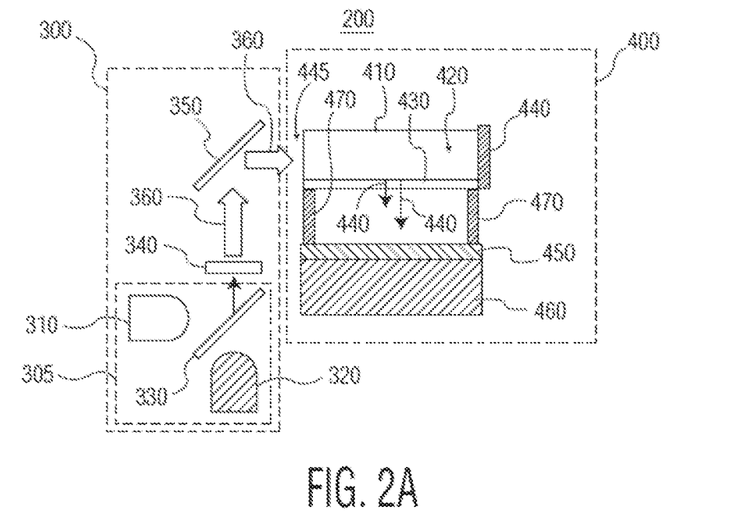
FIG. 2A is a schematic diagram of a fluorescence based sensor system, in accordance with one preferred embodiment of the present invention.

FIG. 2A is a schematic diagram of a fluorescence based sensor system 200, in accordance with one preferred embodiment of the present invention. The system 200 includes an excitation source 300 and a sensor 400. The excitation source 300 preferably includes a light source 305, an excitation filter 340 and mirror 350.

The sensor 400 preferably includes a fluorescence based sensing medium 410 that is contained a recessed cavity 420. The recessed cavity 420 has a transparent bottom surface 430 that transmits fluorescence light from the fluorescence based sensing medium 410, and reflective sides 440 for reflecting unabsorbed excitation light 360 back towards the fluorescence based sensing medium 410. The reflective sides 440 allow for more uniform excitation of the fluorescence based sensing medium 410 by the excitation light 360. All sides of the recessed cavity 420 are preferably reflective, except for an opening 445 that allows excitation light 360 to enter the recessed cavity 420 and the fluorescence based sensing medium 410.

The resulting fluorescence 440 propagates through the transparent bottom surface 430 to emission filter 450, which is preferably a band-pass filter that passes wavelengths of 550 nm±20 nm. The filtered fluorescence light is detected by detector 460, which is preferably a photodiode. The detector 460 is preferably shielded from outside light by a barrier 470, which is preferably formed from a black material (e.g., black plastic, anodized aluminum, etc.) and attached to the transparent bottom surface 430 and the emission filter 450, suitably with temporary glue or held in place with mechanical means (e.g., clamp, elastic band, etc.).

Figures 2B, 2C:
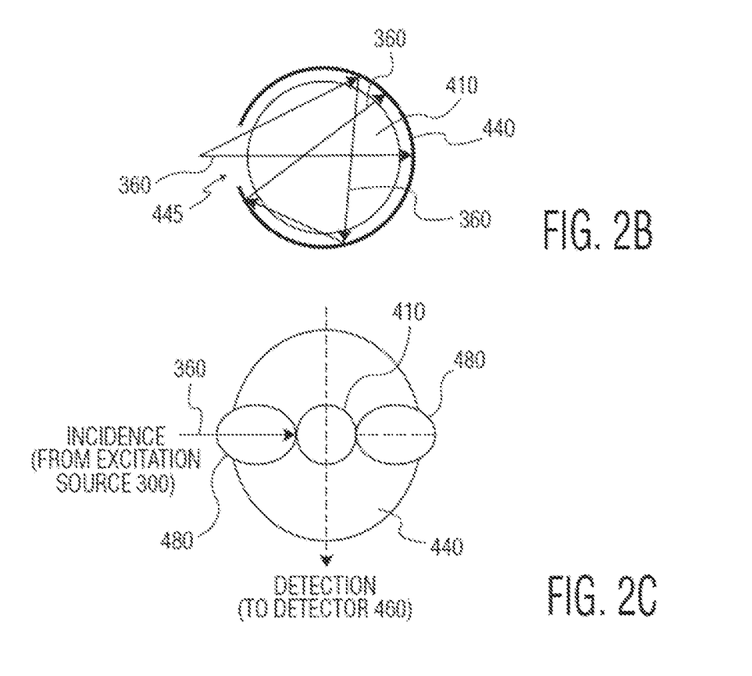
FIG. 2B is a top view of the sensor of FIG. 2A, in accordance with one preferred embodiment of the present invention.
FIG. 2C is a schematic diagram showing the distribution of scattered excitation light and fluorescence light for the system of FIG. 2A.

The fluorescence based sensing medium 410 and recessed cavity 420 are preferably cylindrically-shaped, as shown in the top view of FIG. 2B. This geometry maximizes the uniformity of the distribution of excitation light 360 in the fluorescence based sensing medium 410. FIG. 2C is a schematic diagram showing the scattered light distribution 480 for the sensor 400. As can be seen, substantially no scattered light propagates towards the detector 460.

The system 200 may be adapted as any type of fluorescence based sensing system such as, for example, a pH sensing system or a $CO_2$ sensing system. The light source 305, fluorescence based sensing medium 410 and emission filter 450 are chosen based on the parameter being measured. The system 200 of FIG. 2A can be used to measure both pH and $CO_2$.

For a pH sensing system, the light source 305 preferably includes a blue LED 310, preferably with an emission maximum at approximately 470 nm, a violet LED 320, preferably with an emission maximum at 400 nm, and a dichroic beam splitter 330 for reflecting the light from the blue LED 310 and transmitting the light from the violet LED 320. This is because the operational principal of a fluorescence based pH sensor requires detection of fluorescence emission when the fluorescence based sensing medium 410 is illuminated at two different wavelengths to find their ratio. The emission filter 450 for a pH sensing system is preferably a band-pass filter that passes wavelengths of 550 nm±20 nm.

The excitation filter 340 for a pH sensing system preferably pass wavelengths between approximately 400 nm and 480 nm and absorb wavelengths outside of that range. Excitation light 360 transmitted by the excitation filter 340 is directed to the sensor 400 by mirror 350.

Optical pH detection is based on indicator dyes. A successful example is a pH sensor medium based on an excitation ratiometric fluorescent dye. As such, 8-hydroxypyrene-1,3,6-trisulfonic acid trisodium salt (HPTS) sensor may be suitably used for the fluorescence based sensing medium 410. HPTS exhibits very high photochemical stability and can be polled at two excitation wavelengths that correspond to the protonated and deprotonated form. It is suitable for ratiometric measurements, which is another method for elimination of the inherent drawbacks of intensity-based measurements. Excitation maxima are at 405 and 455 nm, which allows excitation by ultraviolet (UV) and blue LEDs.

The ratiometric determination using excitation ratiometry of a fluorescent dye is described by the following relationship:

$$R = \frac{I_{\lambda_1} \cdot \phi_{\lambda_1} \cdot \varepsilon_{\lambda_1} \cdot [Ind^-]}{I_{\lambda_2} \cdot \phi_{\lambda_2} \cdot \varepsilon_{\lambda_2} \cdot [H-Ind]} \quad (1)$$

Here, $I_{\lambda_1}$ and $I_{\lambda_2}$ are the light intensities at excitation wavelengths $\lambda_1$ and $\lambda_2$, $\phi_1$ and $\phi_2$ are the quantum yields of the luminophore at these wavelengths, $\varepsilon_1$ and $\varepsilon_2$ are the respective molar absorptivities, [H-Ind] is the concentration of undissociated dye, and [Ind$^-$] is the concentration of the dissociated dye. Recalling that [H-Ind]+[Ind$^-$]=[T], where [T] is the total amount of the indicator in the sensor (it is known and constant due to immobilization), it is easy to establish the calibration function of the sensor.

One feature of our measurement technique employed in the sensing system 200 of the present invention is the use of an excitation ratiometric approach. It is especially valuable from a stability point of view. As a result, the chemical portion that the sensor system 200 is based on (the fluorescence based sensing medium 410) is practically insensitive to changes in temperature. However, the optoelectronics (e.g., the LEDs 310 and 320) are still temperature sensitive. The output light intensity from the LEDs 310 and 320 depends on their temperature when turned on. Their output light intensity experiences a decrease of ~3-6% due to self-heating. The decrease depends on the current through the LEDs 310 and 320, the heat resistance of the package and the ambient temperature. As two different LEDs 310 and 320 are used for excitation, their heating profile is different. Although one approach to alleviate this drift would be to leave the LEDs 310 and 320 on constantly, this will lead to an unacceptable power drain, especially for long term autonomous applications. Therefore, the LEDs 310 and 320 are preferably used under stabilized conditions with light-intensity-compensating feedback in the instrumentation.

One application of the present invention is ocean monitoring. Some preliminary research has been done to identify a fluorescent dye with the best properties for ocean monitoring. Three pH sensitive fluorescent dyes, 8-hydroxypyrene-1,3,6-trisulfonic acid trisodium salt (HPTS, pKa=7.3), 6,8-dihydroxy-1,3-pyrenedisulfonic acid disodium salt (DHDS, pKa=7.3), and 5-(and-6)-carboxynaphthofluorescein mixed isomers (CNF, pKa=7.6) have been compared. The measurements were conducted using a Cary Eclipse (Varian) laboratory spectrometer.

Although all three of the dyes have approximately the same sensitivity to $pCO_2$ and can achieve a similar precision, DHDS tends to polymerize and precipitate in carbonate buffered saline while CNF has a poor solubility in neutral pH or acidic solutions. Because stability is one of most important considerations for autonomous ocean sensor, HPTS is also preferably used as the fluorescent dye for $CO_2$ sensing applications.

Figure 3:
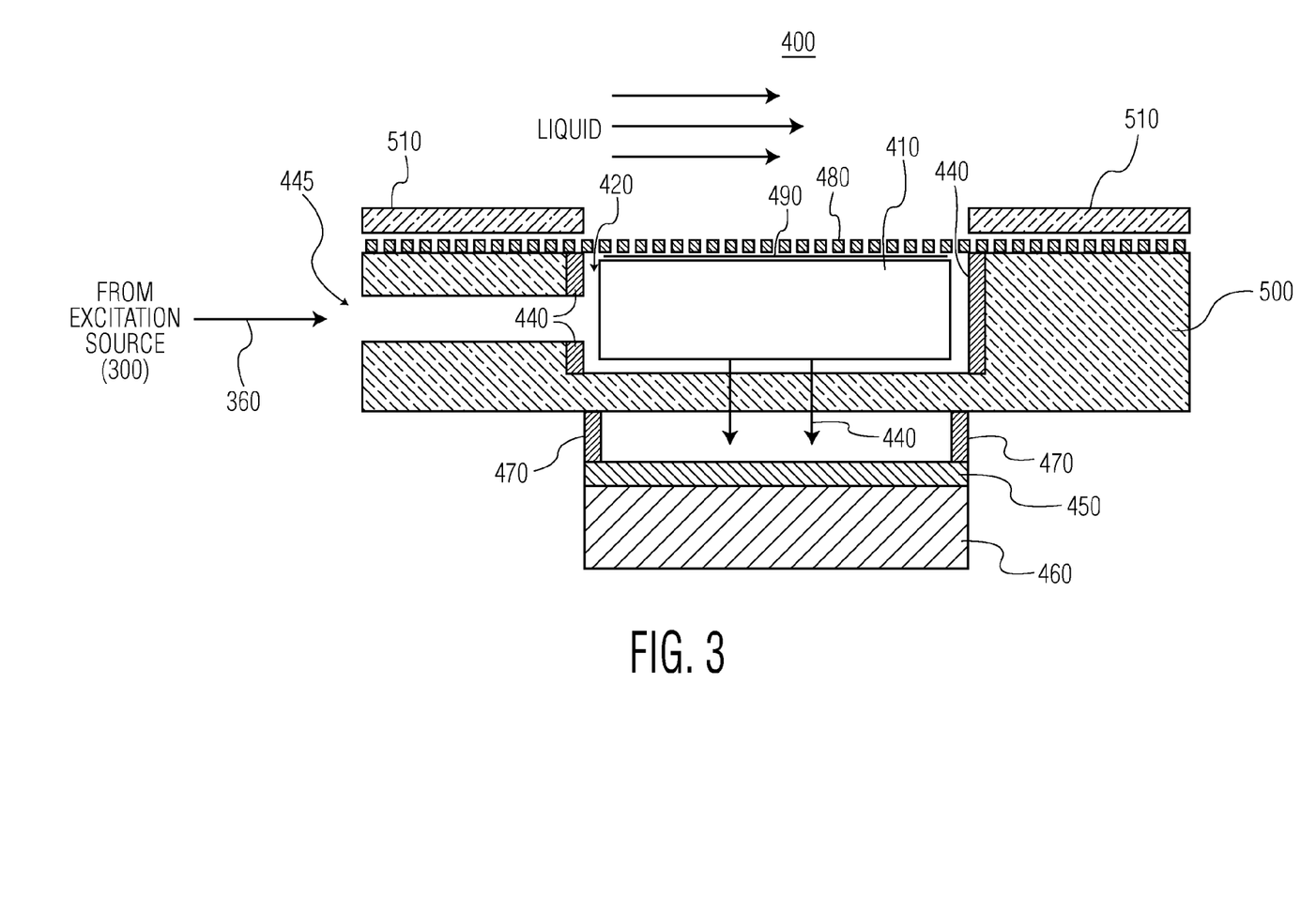
FIG. 3 is a schematic diagram of a sensor for ocean monitoring, in accordance with one preferred embodiment of the present invention.

For ocean pH monitoring, sensitivity and stability are major concerns. To increase the signal/noise ratio, the geometry shown in FIG. 3 is preferably used for the sensor 400. The fluorescence based sensing medium 410 is preferably a pH patch that is preferably approximately 1 mm thick, and the hydrogel precursor is polymerized directly without a supporting matrix so that the resulting pH patch 410 is transparent.

The patch 410 is placed in the recessed mirrored cavity 420 described above, and is preferably covered with a biofouling resistant copper mesh 480 to keep the patch 410 in place. A lid 510 keeps the mesh 480 in place. Optical isolation can optionally be provided for the patches, preferably in the form of a thin white filter paper layer 490 under the mesh 480 if high turbidity/chlorophyll levels are found to affect pH readings. The housing 500 in which the mirrored recessed cavity 420 is formed is transparent to the fluorescence wavelengths of the pH sensing patch 410. Although the sensor 400 shown in FIG. 3 is particularly suited for monitoring of oceans or other large bodies of water, it can also be used for monitoring pH, $CO_2$ or other parameters in a liquid medium of a bioreactor.

The housing 500 and lid 510 are preferably made of transparent material, such as poly(methylmethacrylate), PETG, polystyrene, etc. The lid 510 is preferably attached to the mesh 480 and the housing 500 by any transparent pressure-sensitive adhesive. It can be silicone-based or acrylic-based (e.g., 9770 adhesive from 3M). The reflective sides 440 of the recessed cavity 420 are preferably formed by silvering them using Tolen's reaction (the same process used in making silver mirrors on glass or plastic substrates).

Figure 4:
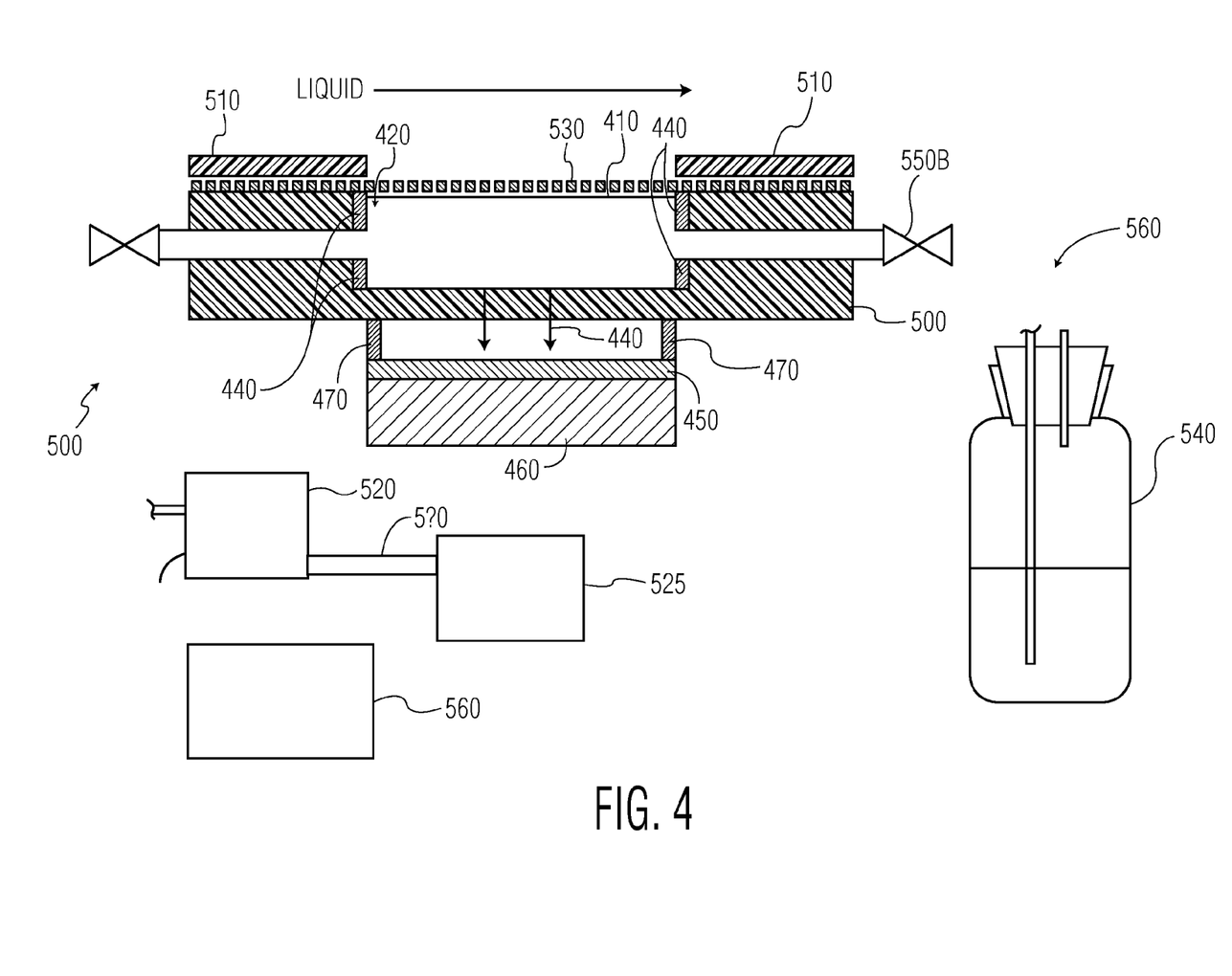
FIG. 4 is a schematic diagram of a sensor for ocean monitoring, in accordance with another preferred embodiment of the present invention.

For ocean $CO_2$ monitoring, the sensitivity of the measurement should be more than 100 times greater and operate at a much lower range than current sensors. One way to maintain the requisite sensitivity over time is to use an automated system that generates a fresh sensor "patch" in situ for the sensor 400. Such a system is shown in FIG. 4.

Figure 5:
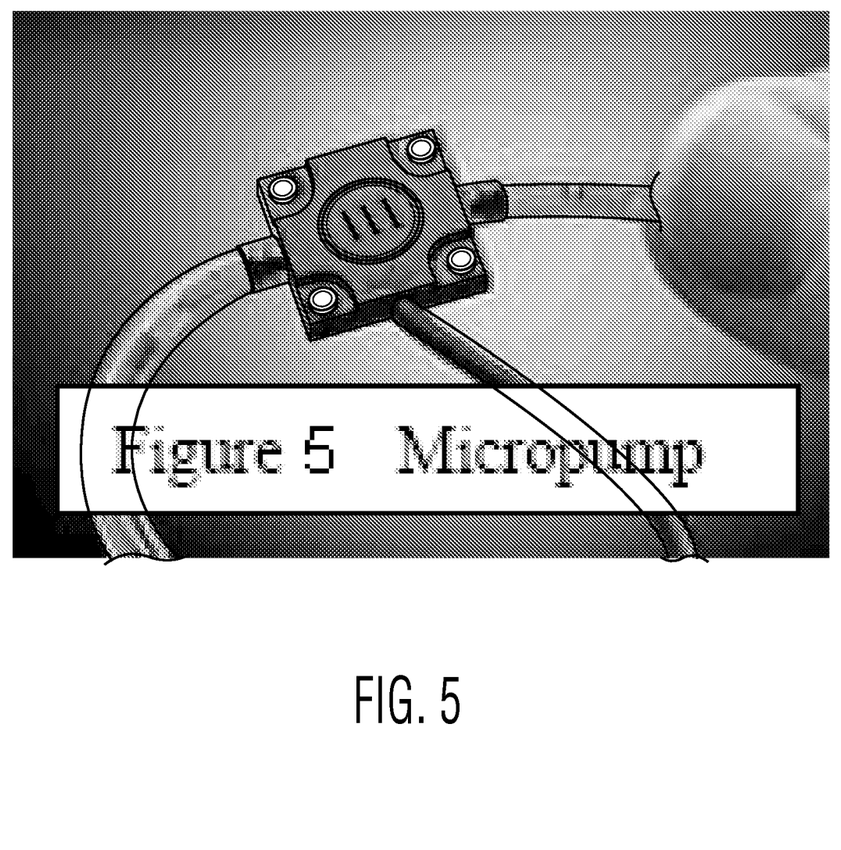
FIG. 5 is a preferred micropump used in the sensor of FIG. 4.

In this embodiment, a pump 520, preferably a micropump such as the one shown in FIG. 5, is programmed to input a fresh aliquot of sensor dye 410 from a reservoir 525 into the sensing patch recess 420. A $CO_2$ diffusing membrane 530 is stretched over the recess 420 to permit $CO_2$ from the ocean to diffuse into the recess 420 and affect a change in the excitation spectrum. A waste chamber collection bottle 540 is used downstream to collect spent dye. Two check-valves 550A and 550B are used to keep the recess 420 sealed off from the pump 520 and waste bottle 540. A bubble trap (not shown) may be employed if necessary. A controller 560 controls the pump 520 to inject new dye 410 into the recess 420 at predetermined time intervals.

The sensing solution 410 preferably contains 1-10 µM of HPTS in 100-1000 µM Na2CO3. The total volume of the recess 420 (Φ5°—2 mm) and the tubing 560 (Φ0.5°—300 mm) is preferably approximately 100 µL. As a worst-case analysis, one can assume that a fresh sensor "patch" 410 is required for every single measurement. If the system is flushed using twice, the total volume for one day of sampling will require approximately 5 ml of the sensing solution.

During operation, the recess 420 is preferably flushed with 200 μL of the sensing dye 410 twenty minutes before each measurement and the fluorescence intensities are measured as soon as possible to get an initial reading. Preferably, twenty minutes later after $CO_2$ diffusion across the membrane 530 and equilibrium is reached, the fluorescence intensities are measured again. From the changes in the fluorescence intensities, the $pCO_2$ level in the water can be calculated. The actual life of each "patch" 410 can be measured and replaced once drift exceeds specifications. When a fresh "patch" 410 is generated after exhaustion of the previous one, very little to no drift at all is expected.

The foregoing embodiments and advantages are merely exemplary, and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. Various changes may be made without departing from the spirit and scope of the invention, as defined in the following claims. For example, although the present sensor system has been described in connection with a pH and $CO_2$ sensing system, it can be applied to any fluorescence based sensing system. Further, although the sensors of FIGS. 3 and 4 have been described as being particularly suited for monitoring large bodies of water, such as oceans and lakes, they can be used to monitor parameters in any type of liquid media, such as liquid media inside a bioreactor.

What is claimed is:

1. A fluorescence based sensor for measuring at least one parameter of a medium, comprising:
    a fluorescence based sensing medium having a top surface, a bottom surface and at least one side surface, wherein the fluorescence based sensing medium exhibits fluorescence properties that vary when the fluorescence based sensing medium comes into contact with the at least one parameter being measured;
    a reflective surface adjacent to the at least one side surface of the fluorescence based sensing medium, wherein the reflective surface is positioned to reflect excitation light that enters the fluorescence based sensing medium through the at least one side surface and that passes through the fluorescence based sensing medium back into the fluorescence based sensing medium such that at least some of the excitation light passes through the fluorescence based sensing medium and is reflected back into the fluorescence based sensing medium at least two times; and
    a detector positioned to detect fluorescence emissions that exit through one of either the bottom or top surface of the fluorescence based sensing medium.

2. The sensor of claim 1, wherein the fluorescence based sensing medium is cylindrically shaped.

3. The sensor of claim 2, wherein the reflective surface extends around at least a portion of the circumference of the cylindrically shaped fluorescence based sensing medium.

4. The sensor of claim 3, wherein the reflective surface contains an opening for allowing excitation light to enter the cylindrically shaped fluorescence based sensing medium through said at least one side surface.

5. The sensor of claim 1, wherein the fluorescence based sensing medium comprises a patch.

6. The sensor of claim 1, wherein the fluorescence based sensing medium comprises a liquid.

7. The sensor of claim 1, further comprising an emission filter positioned between the fluorescence based sensing medium and the detector for transmitting fluorescence light from the fluorescence based sensing medium and blocking at least some light that is not fluorescence light.

8. The sensor of claim 1, wherein the fluorescence based sensing medium comprises an 8-hydroxypyrene-1,3,6-trisulfonic acid trisodium salt (HPTS).

9. The sensor of claim 8, further comprising an emission filter positioned between the fluorescence based sensing medium and the detector, wherein the emission filter passes wavelengths of 550 nm±20 nm.

10. The sensor of claim 1, further comprising a light barrier positioned between the fluorescence based sensing medium and the detector, wherein the barrier has a shape adapted to pass fluorescence emissions from the fluorescence based sensing medium and block ambient light that does not originate from the fluorescence based sensing medium.

11. The system of claim 1, further comprising:
    an excitation source for generating excitation light and directing the excitation light towards a side surface of the fluorescence based sensing medium.

12. The system of claim 11, wherein the excitation source comprises:
    a light source; and
    an excitation filter positioned to receive light from the light source for transmitting light at excitation wavelengths of the fluorescence based sensing medium and blocking at least some of the light at other wavelengths.

13. The system of claim 11, wherein the light source comprises:
    a first LED that emits light with a first spectrum;
    a second LED that emits light with a second spectrum that is different than the first spectrum; and
    a dichroic beam splitter positioned to reflect light from the first LED and transmit light from the second LED.

14. The system of claim 13, wherein the first LED has an emission maximum at 470 nm and the second LED has an emission maximum at 400 nm.

15. A fluorescence based sensor for measuring at least one parameter of a medium, comprising:
    a housing;
    a recessed cavity formed in the housing, wherein at least one of the sides of the recessed cavity are reflective;
    a fluorescence based sensing medium positioned in the recessed cavity, wherein the fluorescence based sensing medium exhibits fluorescence properties that vary when the fluorescence based sensing medium comes into contact with the at least one parameter being measured;
    an opening in the housing that extends from a side surface of the housing to the recessed cavity for allowing excitation light originating outside the housing to enter the fluorescence based sensing medium in the recessed cavity via the opening, wherein the at least one reflective side of the recessed cavity is configured such that at least some of the excitation light that passes through the fluorescence based sensing medium is reflected back into the fluorescence based sensing medium;
    a detector positioned to detect fluorescence emissions that exit through a bottom surface of the fluorescence based sensing medium; and
    a copper mesh layer covering the fluorescence based sensing medium and the recessed cavity;
    wherein the housing material between the fluorescence based sensing medium and a bottom surface of the housing is at least partially transparent to fluorescence emissions from the fluorescence based sensing medium, and wherein the housing is configured to allow the at least one parameter being measured to come into contact with the fluorescence based sensing medium.

16. The sensor of claim 15, wherein the fluorescence based sensing medium and the recessed cavity is cylindrically shaped.

17. The sensor of claim 16, wherein an internal surface of the cylindrically shaped recessed cavity is reflective.

18. The sensor of claim 15, wherein the fluorescence based sensing medium comprises a patch.

19. The sensor of claim 15, further comprising an emission filter positioned between the fluorescence based sensing medium and the detector for transmitting fluorescence light from the fluorescence based sensing medium and blocking at least some light that is not fluorescence light.

20. The sensor of claim 15, wherein the fluorescence based sensing medium comprises an 8-hydroxypyrene-1,3,6-trisulfonic acid trisodium salt (HPTS).

21. The sensor of claim 20, further comprising an emission filter positioned between the fluorescence based sensing medium and the detector, wherein the emission filter passes wavelengths of 550 nm±20 nm.

22. The sensor of claim 15, further comprising a light barrier positioned between the bottom surface of the housing and the detector, wherein the barrier has a shape adapted to pass fluorescence emissions from the fluorescence based sensing medium and block ambient light that does not originate from the fluorescence based sensing medium.

23. A fluorescence based sensor for measuring at least one parameter of a medium, comprising:
- a housing;
- a recessed cavity formed in the housing, wherein at least one of the sides of the recessed cavity are reflective;
- a fluorescence based sensing medium positioned in the recessed cavity, wherein the fluorescence based sensing medium comprises a liquid and exhibits fluorescence properties that vary when the fluorescence based sensing medium comes into contact with the at least one parameter being measured;
- an opening in the housing that extends from a side surface of the housing to the recessed cavity for allowing excitation light originating outside the housing to enter the fluorescence based sensing medium in the recessed cavity via the opening, wherein the at least one reflective side of the recessed cavity is configured such that at least some of the excitation light that passes through the fluorescence based sensing medium is reflected back into the fluorescence based sensing medium;
- a detector positioned to detect fluorescence emissions that exit through a bottom surface of the fluorescence based sensing medium;
- a reservoir for holding liquid fluorescence based sensing media;
- a waste container in fluid communication with the recessed cavity for receiving discarded liquid fluorescence based sensing media from the recessed cavity; and
- a pump in fluid communication with the reservoir and the recessed cavity for replacing existing liquid fluorescence based sensing media in the recessed cavity with new liquid fluorescence based sensing media from the reservoir by pumping the new fluorescence based sensing media into the recessed cavity, thereby displacing the existing liquid fluorescence based sensing medium into the waste container;
- wherein the housing material between the fluorescence based sensing medium and a bottom surface of the housing is at least partially transparent to fluorescence emissions from the fluorescence based sensing medium, and wherein the housing is configured to allow the at least one parameter being measured to come into contact with the fluorescence based sensing medium.

24. The sensor of claim 23, wherein the fluid communication between the pump, the reservoir, the recessed cavity and the waste container is provided by tubing between the reservoir and the pump, between the pump and the housing and between the housing and the waste container.

25. The sensor of claim 24, further comprising a check valve between the pump and the housing and a check valve between the housing and the waste container for selectively isolating the recessed cavity from the pump and waste container.

26. The sensor of claim 23, further comprising a controller in electrical communication with the pump configured to control the pump to replace the liquid fluorescence based sensing media in the recessed cavity at time intervals set by a user or in response to a command sent by a user.

* * * * *